US00PP22095P3

(12) United States Plant Patent
Holland et al.

(10) Patent No.: US PP22,095 P3
(45) Date of Patent: Aug. 30, 2011

(54) APRICOT TREE NAMED 'DANIEL'

(50) Latin Name: *Prunus armeniaca*
Varietal Denomination: Daniel

(75) Inventors: Doron Holland, Hasolelim (IL); Irit Bar-Ya'akov, Qiryat Tivon (IL); Kamel Hatib, Arrabe (IL); Amnon Erez, Rehovot (IL); Ze'ev Yablovitz, Rehovot (IL); Raya Korchinsky, Rishon Le-Zion (IL)

(73) Assignee: State of Israel, Ministry of Agriculture & Rural Development, Agricultural Research Organization, Bet Dagan (IL)

( * ) Notice: Subject to any disclaimer, the term of this patent is extended or adjusted under 35 U.S.C. 154(b) by 152 days.

(21) Appl. No.: 12/462,238

(22) Filed: Jul. 31, 2009

(65) Prior Publication Data

US 2011/0030110 P1 Feb. 3, 2011

(51) Int. Cl.
*A01H 5/00* (2006.01)

(52) U.S. Cl. ..... Plt./186

(58) Field of Classification Search ..... Plt./186
See application file for complete search history.

(56) References Cited

OTHER PUBLICATIONS

Print-out of application number and filing date information for corresponding IL PBR application No. 3999/07 filed Mar. 14, 2007, published by the Ministry of Agriculture & Rural Development in Israel PBR Gazette No. 69, Jan. 1, 2007-Jun. 30, 2007 (3 pages). (http://www.moag.gov.il/NR/rdonlyres/DA946C0C-4AA5-4A6A-8B31-D8A43DBAC5DF/0/1176gazette69_160807.pdf).
Print-out of application number and filing date information from Community Plant Variety Office (CPVO) website for corresponding, CPVO application No. 2007/2595 filed Nov. 26, 2007 (6 pages). (http://www.cpvoextranet.cpvo.europa.eu).

*Primary Examiner* — Wendy Haas
(74) *Attorney, Agent, or Firm* — Foley & Lardner LLP

(57) ABSTRACT

A new and distinct apricot variety of *Prunus armeniaca* named 'DANIEL', particularly characterized by self-pollinating and self-fertile medium-sized tree with vigorous growth habit; good fruit productivity; early ripening with harvest of mature fruit in early May in Yizre'el Valley, Israel; medium-sized, freestone mature fruit, with deep orange skin color; and aromatic mature fruit which is of good eating quality(sweet-sour flavor, firm texture and moderate juice production).

6 Drawing Sheets

Latin name of the genus and species of the plant claimed: *Prunus armeniaca.*

Variety denomination: 'DANIEL'.

BACKGROUND OF THE INVENTION

The present invention relates to a new and distinct variety of apricot tree, botanically known as *Prunus armeniaca* L. of the Rosaceae family, and hereinafter referred to by the variety denomination 'DANIEL'.

The new *Prunus armeniaca* variety is a product of a controlled breeding program conducted by the inventors, Doron Holland, Irit Bar-Ya'akov, Kamel Hatib, Amnon Erez, Ze'ev Yablovitz and Raya Korchinsky in Yizre'el Valley, Israel. The objective of the breeding program was to develop a new *Prunus armeniaca* variety with an early ripening period of mature fruit and vigorous production of mature fruit with good eating quality.

The new *Prunus armeniaca* variety originated in 1999 from open-pollination by an unknown *Prunus armeniaca* L. variety of the early-ripening *Prunus armeniaca* L. variety 'TAROG' (Registered in Israel for Plant Breeder's Rights, No. 2441 dated 15 Mar. 2005). The new *Prunus armeniaca* variety 'DANIEL' was discovered and selected by the inventors as a unique and promising seedling resulting from the above self-pollination in 2006 in a controlled environment in Yizre'el Valley, Israel.

Asexual reproduction of the new *Prunus armeniaca* 'DANIEL' by grafting onto plum rootstock designated Marianna '26-24' (unpatented) and apricot rootstock designated 'KLABI' (unpatented), was first performed in February of 2006 in the Yizre'el Valley of Israel, and has demonstrated that the combination of characteristics as herein disclosed for the new variety are firmly fixed and retained through successive generations of asexual reproduction. The new variety reproduces true to type. Resulting trees of new *Prunus armeniaca* 'DANIEL' were planted in 2007 in the Yizre'el Valley and the central coastal region of Israel.

BRIEF SUMMARY OF THE INVENTION

The following traits have been repeatedly observed and are determined to be unique characteristics of 'DANIEL' which in combination distinguish this apricot tree as a new and distinct variety:

1. self-pollinating and self-fertile medium-sized tree with vigorous growth habit;
2. good fruit productivity;
3. early ripening with harvest of mature fruit in early May in Yizre'el Valley and central coastal region of Israel;
4. medium-sized, freestone mature fruit, with deep orange skin color; and
5. aromatic mature fruit which is of good eating quality (sweet-sour flavor, firm texture and moderate juice production).

In comparison to the parental variety, *Prunus armeniaca* 'TAROG' (Registered in Israel for Plant Breeder's Rights, No. 2441 dated 15 Mar. 2005), the new *Prunus armeniaca* 'DANIEL' differs primarily in the traits listed in Table 1.

TABLE 1

| Trait | New Variety 'DANIEL' | Parental Variety 'TAROG' (Israel Plant Breeder's Rights No. 2441 dated 15 Mar. 2005) |
|---|---|---|
| Ripening Time | Earlier than 'TAROG' (beginning of May in Israel) | Later than 'DANIEL' (middle of May in Israel) |
| Fruit Skin Color | Lighter orange than 'TAROG' | Darker orange than 'DANIEL' |
| Fruit Shape | Moderately flattened | Slightly flattened |

Of the many commercial varieties known to the present inventors, the most similar in comparison to the new *Prunus armeniaca* 'DANIEL' is the parental variety 'TAROG', as described in the foregoing Table 1.

BRIEF DESCRIPTION OF THE PHOTOGRAPHS

The accompanying photographs illustrate the overall appearance of the new *Prunus armeniaca* 'DANIEL' showing the colors as true as is reasonably possible with colored reproductions of this type. Colors in the photographs may differ slightly from the color values cited in the detailed botanical description, which accurately describe the color of 'DANIEL'.

DETAILED DESCRIPTION OF THE INVENTION

Figure 1:
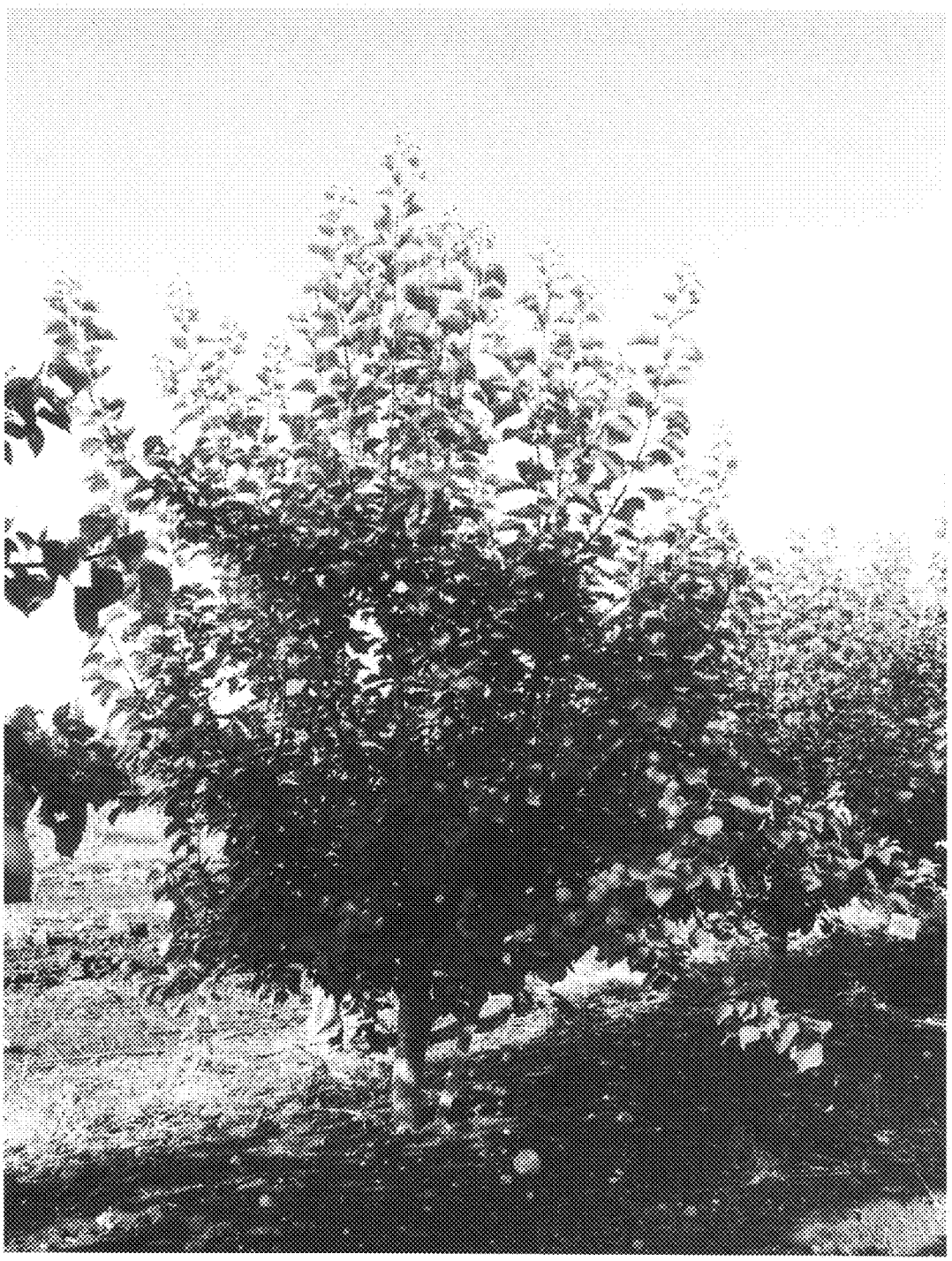
FIG. 1 shows a side view perspective of a typical 16 month old whole tree of 'DANIEL', grafted on 'KLABI' rootstock (unpatented).
Figure 2:
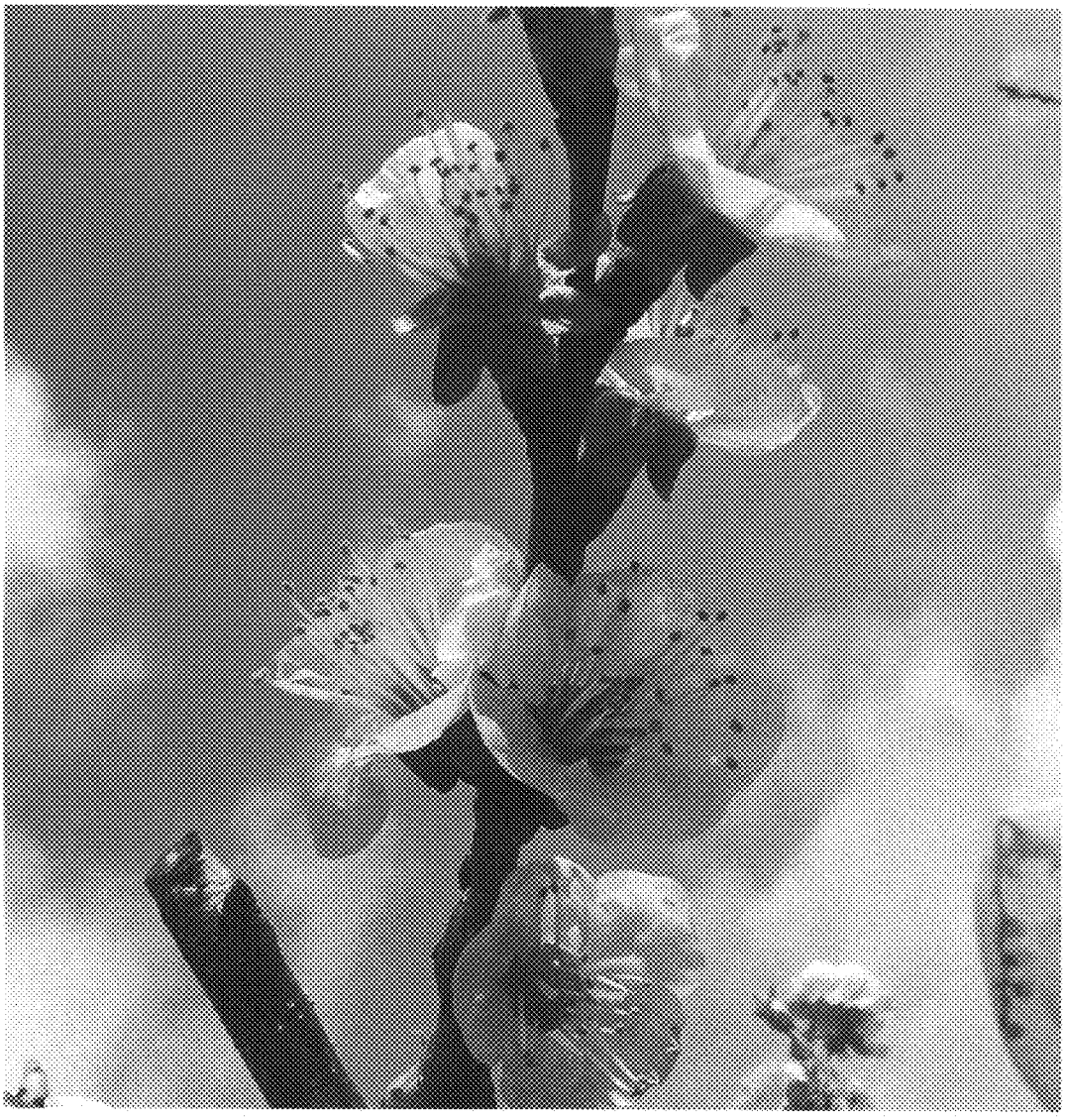
FIG. 2 shows a side view perspective of typical flowers on a branch of 'DANIEL' while in bloom.
Figure 3:
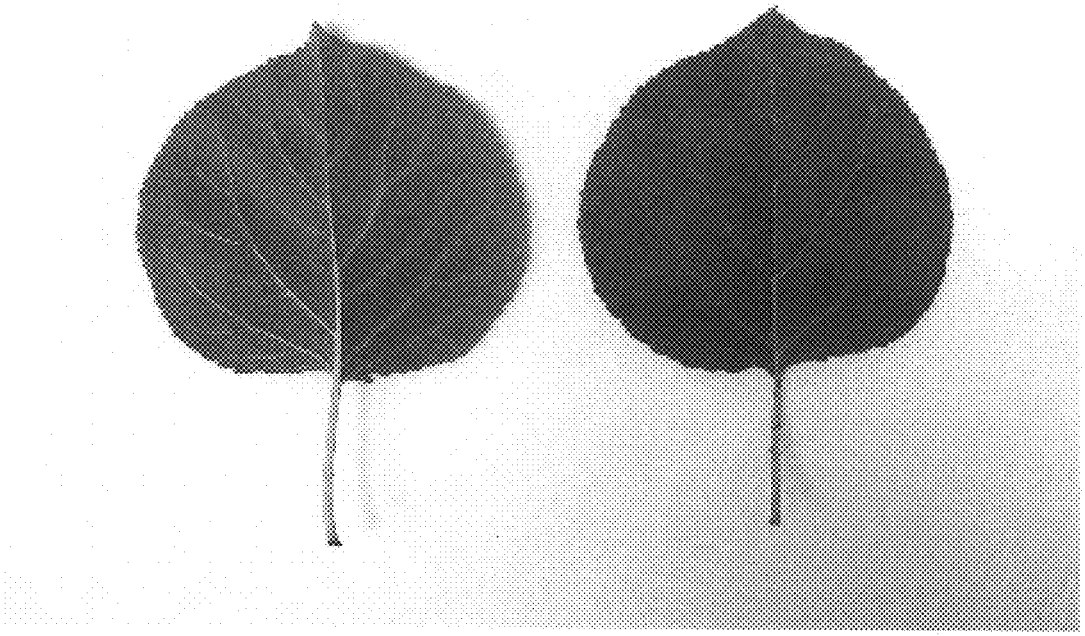
FIG. 3 shows a close-up view of the upper and under surfaces of typical leaves of 'DANIEL'.
Figure 4:
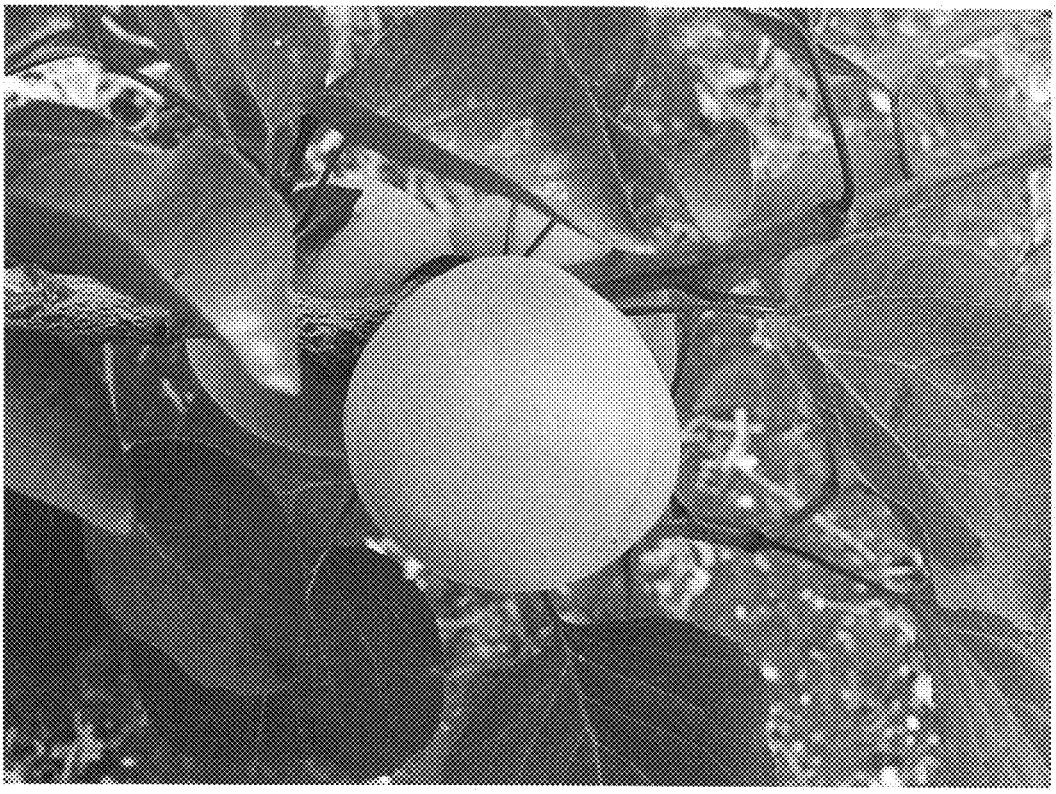
FIG. 4 shows a close-up view of typical fruit on a branch of 'DANIEL'.
Figure 5:
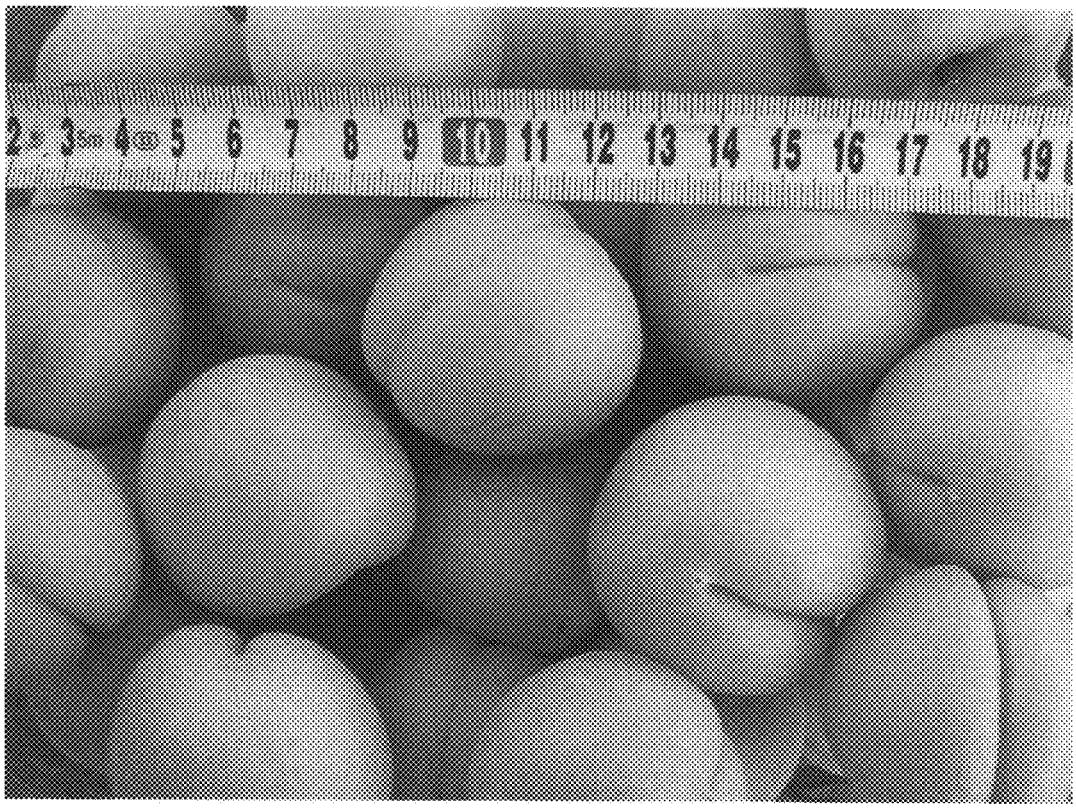
FIG. 5 shows a perspective view of typical mature fruit of 'DANIEL' in a (14×24 cm) size shipping box.
Figure 6:
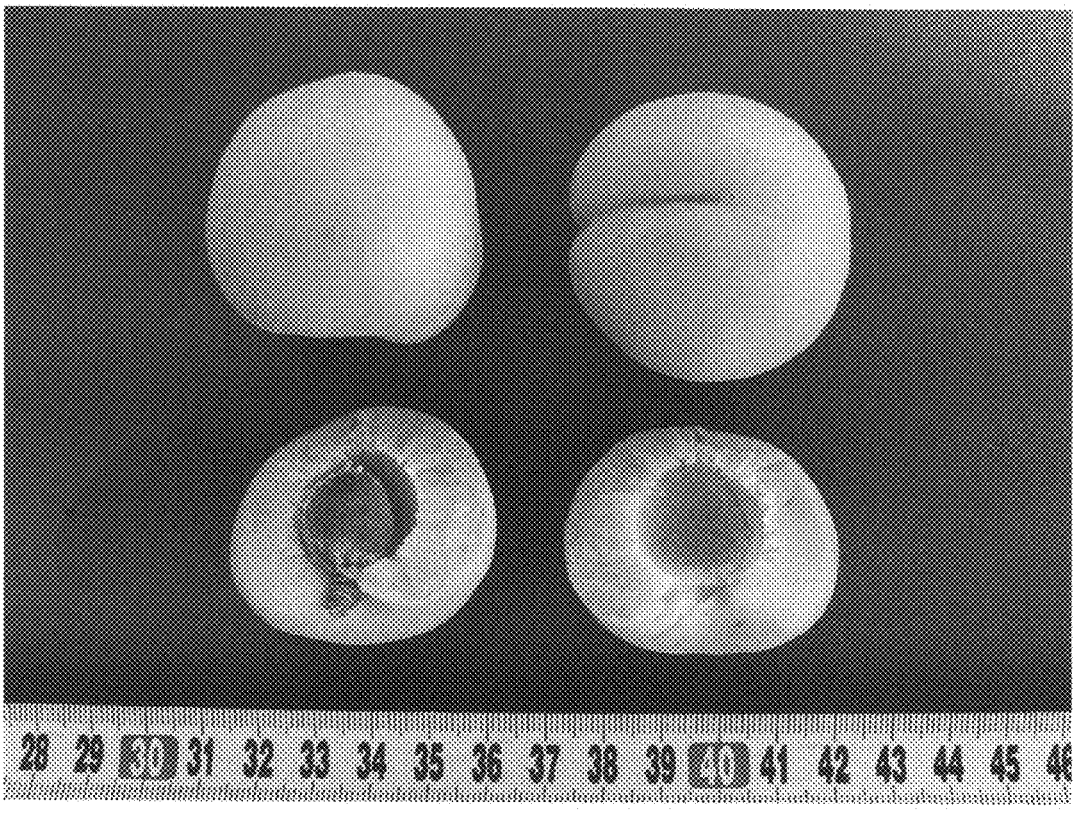
FIG. 6 shows various close-up views of typical mature fruit of 'DANIEL', illustrating the typical skin and flesh color, shape, pit cavity and the pit.

The new *Prunus armeniaca* 'DANIEL' has not been observed under all possible environmental conditions. The phenotype of the new variety may vary with variations in environment such as temperature, light intensity, and day length without any change in the genotype of the apricot tree.

The aforementioned photographs, together with the following observations, measurements and values describe trees of 'DANIEL' as grown in an apricot farm in the Yizre'el Valley of Israel, under conditions which closely approximate those generally used in commercial practice. Seedlings of 'DANIEL' were planted mainly in clay grumusol (vertisol) soil at an elevation of about 100 meters above sea level, at lat. 32° 42'N, long. 35° 11'E. Yizre'el Valley is characterized by a Mediterranean subtropical climate, with an average annual rainfall of about 580 mm concentrated from November through March. Mean diurnal minimum temperature in January is 6° C. (43° F.), and mean diurnal maximum temperature in July is 33° C. (91° F.).

Unless otherwise stated, the detailed botanical description includes observations, measurements and values based on two year old 'DANIEL' trees grown in the apricot farm in Yizre'el Valley, Israel from 2007 to 2008. Quantified measurements are expressed as an average of measurements taken from a number of trees of 'DANIEL'. The measurements of any individual tree, or any group of trees, of the new variety may vary from the stated average.

Color references are made to The Royal Horticultural Society Colour Chart (R.H.S.), 2001 edition, except where general colors of ordinary significance are used. Color values were taken under daylight conditions at approximately (late morning) in Yizre'el Valley, Israel.

All of the trees of 'DANIEL', insofar as they have been observed, have been identical in all the characteristics described below.

Classification:

*Botanical.*—*Prunus armeniaca* L.

Parentage:

*Seed parent.*—*Prunus armeniaca* L. 'TAROG' (Registered in Israel for Plant Breeder's Rights, No. 2441 dated 15 Mar. 2005).

*Pollen parent.*—Open-pollination by unknown *Prunus armeniaca* L. variety.

Propagation: Grafting onto plum rootstock designated Marianna '26-24' (unpatented) and apricot rootstock designated 'KLABI' (unpatented).

Growing conditions:

*Light intensities.*—Full sunlight or slight shade.

*Fertilization.*—A level of about 250 Kg/ha N and 300 Kg/ha K per year.

*Growth regulators.*—Not used.

*Pruning or trimming requirements.*—Winter and summer pruning.

Tree:

*Age.*—Observed trees were two years old.

*Vigor.*—Good vigor; early beginning production; good productivity.

*Form.*—Upright, medium-sized tree with one trunk; somewhat spreading canopy with narrow branch angles.

*Habit.*—A medium-sized tree with a trunk and 3-4 semi-upright main branches forming open crown.

*Branching habit.*—Main branches angle is 45° up to 180° with respect to trunk if allowed to grow naturally.

*Type of bearing.*—Short spurs and long lateral shoots and spurs. On branches fruit bear, on tip, central and base area of branch.

*Production.*—Good.

*Size at maturity.*—Height: About 3.4 m to 3.8 m. Spread: About 2.7 m to 3.2 m (at second leaf).

Trunk:

*Height* (*up to leaders*).—About 50 cm.

*Diameter* (*at* 20 *cm above graft*).—About 30.9 cm±0.9 cm.

*Texture.*—Rough.

*Bark color.*—Greyed-orange, RHS 166A.

*Trunk Lenticels.*—Density: Scattered densely on trunk. Shape: Irregular, elliptic. Length: About 6 mm. Width: About 2 mm. Color: Grey, RHS 201A.

Branches:

*Diameter* (*at two years,* 7 *cm above branching*).—About 20.7 cm±1.3 cm.

*Growth per season.*—Dependent upon prevailing growth conditions and tree management.

*Surface texture.*—New Growth: Smooth. Mature: Nearly smooth to semi-rough.

*Color.*—New Growth: Yellow-green, RHS 144A. Mature: Greyed-orange, RHS 177A.

*Branch lenticels.*—Density: Scattered densely. Shape: Narrowly elliptic. Size (primary, mature branches): Small to medium. Length: About 4 mm to 6 mm. Width: About 2 mm. Size (immature branches): Very Small. Length: About 1 mm to 2 mm. Width: About 1 mm. Color (primary, mature branches): Too small to distinguish RHS value. Color (immature branches): Too small to distinguish RHS value.

Internode:

*Length.*—Average node length on typical 1 year old branch is 1.7 cm.

*Diameter.*—About 10 mm (lower part) to 3 mm (upper part).

Spur: Present.

*Distance between each spur.*—On the two year old branches, 3-4 spurs per 10 cm.

*Number of fruit per spur.*—About 1 to 3 (commercially thinned to 1).

Foliage:

*Arrangement.*—Alternate, simple, petiolated.

*Lamina.*—Size (fully developed lamina): Length: About 87 mm±3 mm. Width: About 80 mm±1 mm. Overall Shape: Ovate. Base shape: Acute. Apex shape: Acuminate. Margin: Crenate. Pubescence: Upper surface: Glabrous. Under surface: Glabrous. Color (mature leaves): Upper surface: Green, RHS 139A. Under surface: Green, RHS 137B. Color (immature leaves): Upper and Under surfaces: Red, RHS 46A. Venation: Type: Pinnate venation from midrib (about 1 mm to 2 mm) to leaf edge. Color: Red midrib, RHS 46, gradually changing to yellow-green, RHS 144A, near apex.

Petiole:

*Length.*—About 35.3 mm±0.7 mm.

*Diameter.*—About 2 mm.

*Texture.*—Smooth.

*Color.*—Red, RHS 46A.

Glands:

*Number.*—About 6 to 10.

*Position.*—Upper side of petiole.

*Form.*—Rounded to Ovate.

*Size.*—Too small to measure.

Stipule: None.

Inflorescence:

*Blooming time.*—Full bloom on about March 8$^{th}$ to March 10$^{th}$ in Yizre'el Valley, Israel.

*Blooming period.*—About 2 to 3 weeks in Yizre'el Valley, Israel.

*Fragrant.*—Yes.

*Inflorescence type.*—Flowers are borne single or clustered.

*Number of flowers per cluster.*—About 2 to 3.

*Inflorescence size.*—Diameter: About 25 mm to 30 mm.

Buds:

*Number per spur.*—Cluster of two or three.

*Shape.*—Rounded, pointed apex.

*Length.*—About 3 mm to 5 mm.

*Width.*—About 3 mm.

*Color.*—Dark red-brown, RHS 183A.

Petals:

*Arrangement.*—Partly overlapping.

*Number per flower.*—Five.

*Size.*—Length: About 10 mm to 13 mm. Width: About 12 mm to 15 mm.

*Overall shape.*—Widely ovate to round.

*Apex shape.*—Round.

*Base shape.*—Truncate, excluding tiny claw.

*Texture* (*upper and under surfaces*).—Smooth.

*Margin.*—Entire, slightly undulate.

*Color.*—Upper surface: White, RHS 155D. Under surface: Light pink, RHS 56D.

Calyx:

*Length.*—About 9 mm to 13 mm.

*Diameter.*—About 10 mm to 13 mm.

*Texture* (*outer and inner surfaces*).—glabrous.

Sepals:

*Number per flower.*—Five.

*Size.*—Length: About 4 mm to 6 mm. Width: About 4 mm to 5 mm.

*Overall shape.*—Elongated.

*Apex shape.*—Rounded.

*Base shape.*—Fused.

*Margin.*—Entire.

*Color.*—Outer surface: At base, orange, RHS 25C; At apex, brown-red, RHS 145D. Inner surface: Orange, RHS 24A.

Pedicle:

*Length.*—About 1 mm.

*Diameter.*—Less than 1 mm.

*Texture.*—Smooth.

Fruit:

*Keeping quality.*—The fruit keeps for about two weeks on the tree. It can be stored in cold temperature conditions at 5° C. for about one week without losing firmness and juiciness. It has a shelf life of about five days without losing firmness and juiciness depending on the degree of ripening on the tree.

*Maturity when described.*—Ripe for eating.

*Maturity period after full bloom.*—About 55 to 65 days after full bloom on March 8$^{th}$ in Yizre'el Valley, Israel.

*Date of first and last picking* (*harvest*).—Early May, about May 4$^{th}$ in Yizre'el Valley, Israel in 2008.

*Type.*—Drupe.

*General shape.*—Round and flattened.

*Apex shape.*—Pointed, pistil point very small.

*Ventral surface.*—Rounded, lipped, both sides.

*Symmetry.*—Good, nearly symmetrical.

*Suture.*—Intermediate, distinct groove, extending from the base to apex, a little deeper toward stalk cavity.

*Average weight.*—Medium, about 38.5 g±1.1 g.

*Fruit size.*—Diameter of axial plant: About 40.9 mm±0.5 mm. Transverse length in suture plane: About 40.6 mm±0.5 mm. Transverse length in right angle to suture plane: About 40.6 mm±0.6 mm.

Stalk cavity:

*Shape.*—Elliptic.

*Length.*—About 12 mm to 15 mm.

*Diameter.*—About 10 mm to 11 mm.

*Depth.*—About 6 mm to 7 mm.

Stalk:

*Length.*—Short, about 6 mm.

*Diameter.*—About 4 mm.

*Color.*—Light green, RHS 144B, with reddish overcolor, RHS 46A.

Skin:

*Thickness.*—Medium.

*Texture.*—Smooth with fine pubescence.

*Tenacity.*—Adherent to flesh.

*Astringency.*—Absent.

*Tendency to crack.*—None.

*Ground color.*—Orange, RHS N25D.

*Blush color.*—Red, RHS 42B.

*Percentage of skin surface with overcolor color.*—Very little, close to 0%.

Flesh:

*Color at maturity.*—Yellow-orange, RHS 23A.

*Color at maturity* (*when dried*).—N/A, for fresh use only.

*Texture.*—Firm, fine flesh.

*Fibers.*—Moderate number, not noticeable or felt.

*Ripening.*—Uniform.

*Aroma.*—Moderate to rich.

*Eating quality.*—Very good.

*Juice production.*—Moderate.

*Flavor.*—Sweet-sour.

Seed:

*Type.*—Single, freestone.

*Fibers.*—Very little.

*Overall shape* (*lateral view*).—Round.

*Apex shape.*—Mucronate.

*Base shape.*—Rounded.

*Sides.*—Nearly Equal.

*Ventral ridge.*—Extending from base to apex.

*Length.*—About 19.9 mm±0.3 mm.

*Width.*—About 16.6 mm±0.3 mm.

*Surface.*—Rough.

*Stone dry weight.*—About 2.2 g to 2.5 g.

*Average stone wall thickness.*—About 1.0 mm to 1.1 mm.

*Tendency to crack/split.*—None.

*Color.*—External color (when dry): Light brown, RHS 164B. Internal color when cracked: Very light brown, RHS 164C. Cavity color: Yellow-orange, RHS 23A.

Kernel:

*Shape.*—Ovate.

*Size.*—Length: About 13 mm to 16 mm. Width: About 9 mm to 12 mm. Thickness: About 3 mm to 5 mm.

*Skin color.*—Light brown, RHS 165C.

*Vein color.*—Light brown, RHS 165C.

*Endosperm color.*—Off white, RHS 158A.

*Surface.*—Rough with extruding veins.

*Taste.*—Strong, bitterness.

*Hilium length.*—About 4 mm.

Claw: Very small.

Reproductive organs:

Androecium:

*Stamen.*—Number per flower: About 20. Length: About 10 mm. Color: Light yellow-green, closest to RHS 145C.

*Anther.*—Length: About 2 mm. Color: Yellow, RHS 12B.

*Filaments.*—Length: About 7 mm to 12 mm. Color: White, RHS 155D.

*Pollen.*—Amount: Abundant. Color: Yellow, RHS 12B. Pollination Requirements: None, 'DANIEL' self-fertile and self-pollinator.

Gynoecium:

*Pistils.*—Quantity: One. Length: About 11 mm to 16 mm. Color: Very light green, RHS 145D.

*Stigmas.*—Color: Very light green, RHS 145D.

*Ovary.*—Shape: Obovate. Pubescence: Very strong, white, RHS 155D.

Market: Fresh market.

Usage: Dessert fruit.

Disease/pest resistance: No atypical resistance has been noted.

Disease/pest susceptibility: No atypical resistance has been noted.

Winter hardiness: Tolerant to temperatures down to −3° C. without observed damage to wood and buds of dormant Apricot trees.

Drought/heat tolerance: Tolerant to temperatures up to 40° C.

Shipping/storage characteristics: Overall good, shipping and storage with typical resistance to damage.

What is claimed is:

1. A new and distinct apricot variety of *Prunus armeniaca* plant named 'DANIEL', as illustrated and described herein.

* * * * *